United States Patent [19]

Cavazza

[11] 4,371,618
[45] Feb. 1, 1983

[54] PROCESS FOR ENZYMATICALLY PRODUCING L-CARNITINE

[75] Inventor: Claudio Cavazza, Rome, Italy

[73] Assignee: Sigma-Tau Industrie Farmaceutiche Riunite S.p.A., Rome, Italy

[21] Appl. No.: 277,008

[22] Filed: Jun. 24, 1981

[30] Foreign Application Priority Data

Jun. 24, 1980 [IT] Italy ............................. 86253 A/80

[51] Int. Cl.³ ..................... C12P 13/00; C12R 1/645
[52] U.S. Cl. .................................. 435/128; 435/911
[58] Field of Search ............................. 435/128, 106

[56] References Cited

FOREIGN PATENT DOCUMENTS 2398046  3/1979  France ........................ 435/106

*Primary Examiner*—Lionel M. Shapiro
*Attorney, Agent, or Firm*—Bruce M. Collins

[57] ABSTRACT

An enzymatic process for producing L-carnitine is disclosed which comprises contacting a solution in a hydroxyl group donor solvent of γ-butyrobetaine, sodium-2-oxoglutarate, a reducing agent and a ferrous salt as a hydroxylation catalyst with a phase comprising a spore preparation of the mold *Neurospora crassa*.

9 Claims, No Drawings

PROCESS FOR ENZYMATICALLY PRODUCING L-CARNITINE

The present invention relates to a process for producing L-carnitine and more specifically it relates to a process for enzymatically producing L-carnitine by reacting γ-butyrobetaine with a hydroxylase enzyme.

As known, carnitine (β-hydroxy-γ-trimethyl-amino butyric acid) contains a center of asymmetry and thus two stereoisometers, the D and the L form, of carnitine exist.

L-carnitine is normally present in the body where it exerts the function of a carrier of activated long-chain free fatty acids through the mitochondrial membrane. Since the mitochondrial membrane is impermeable to acyl CoA derivatives, long-chain free fatty acids can enter only when esterification with L-carnitine has taken place. The carrier function of L-carnitine is exerted both by transporting active long-chain fatty acids from the sites of their biosynthesis, for example the microsomes, to the mitochondria where they are oxidized, and by transporting acetyl CoA from the mitochondria, wherein it is formed, to the extramitochondrial sites where the synthesis of long-chain fatty acids occurs, e.g. in the microsomes wherein acetyl CoA can be utilized for synthesizing cholesterol and fatty acid.

Whilst the laevorotatory isomer (L-carnitine) exclusively is the biologic form (and in fact, D-carnitine has never been detected so far in mammalian tissues, the D, L-carnitine racemate has been used for a number of years for different indications. For example, D,L-carnitine is sold in Europe as an appetite stimulant, and it has been reported that the material has an effect on the growth rate of children; see e.g. Borniche et al., Clinic Chemica Acta, 5, 171-176, 1960 and Alexander et al., "Protides in the Biological Fluids", 6th Colloquium, Bruges, 1958, 306-310. U.S. Pat. No. 3,830,931 describes improvements in myocardial contractility and systolic rhythm in congestive heart failure which can often be obtained through administration of D, L-carnitine. U.S. Pat. No. 3,810,994 discloses the use of D,L-carnitine in the treatment of obesity.

Recently, however, an increasing concern on the importance of utilizing exclusively the carnitine laevorotatory isomer for at least some therapeutic applications has widely spread. It has, in fact, been shown that D-carnitine is a competitive inhibitor of carnitine-linked enzymes such as carnitine acetyl transferase (CAT) and carnitine palmityl transferase (PTC). Moreover, recent evidence suggests that D-carnitine can deplete the L-carnitine level of heart tissue. Consequently, it is essential that L-carnitine exclusively be administered to patients under medical treatment for heart diseases or lowering of blood lipids.

Several processes have been proposed for producing carnitine on the industrial scale. The chemical synthesis of carnitine unavoidably leads, however, to a racemic mixture of the D and L isomers. Consequently, resolution methods have to be resorted to whereby the separate optical antipodes are obtained from the racemate.

A typical resolution method wherein D,L-carnitinamide hydrochloride is used as the starting compound for resolution is disclosed in the Belgian Pat. No. 660039. Such a process comprises the use of D camphoric acid for producing the D camphorate of D,L carnitinamide. An alcoholic solution of this compound is subjected to fractional crystallization so as to give the L-isomer as the first fraction to precipitate from the solution.

In order to form the D camphorate of D,L carnitinamide, it is first necessary to form the ammonium salt of D camphoric acid with ammonia; the ammonium D camphorate that is formed is then converted to silver D camphorate by the action of silver nitrate. Since the carnitinamide is in the hydrochloride salt form, the formation of this silver salt is essential in order to eliminate the chloride ion. Such a process is, therefore, very expensive (because of the imperative use of the silver compound) and difficult to carry out industrially in that the various steps of the process have to be carried out away from the light in order to avoid marked blackening of the reaction vessels, due to the large quantity of AgCl which is formed. The D camphorate of D,L carnitinamide may in addition be rendered impure by the presence of silver ions.

Moreover, after the D camphorate of L-carnitinamide has been crystallized out of the alcoholic solution, further steps are needed to eventually convert it into L-carnitine.

More recently, in the French patent application No. 77 22 183 an enzymatic process has been disclosed wherein L-carnitine exclusively is synthesized by asymmetrically reducing dehydrocarnitine,

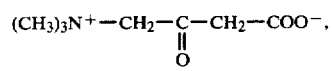

with carnitine dehydrogenase, a coenzyme usable by the dehydrogenase for the reduction such as nicotinamide adenine dinucleotide (NADH), and a chemical or enzyme reagent suitable for reducing the oxydized form of NAD into its reduced form, NADH. The carnitine dehydrogenase is isolated from a bacterium of the genus Psudomonas.

This process, as well as any other process which, with a view to producing pharmaceuticals, is based on the use of bacteria, entails several disadvantages:

1. The enzyme systems must be carefully purified with attendant cumbersome purification procedures and high costs, particularly when the process is carried out on an industrial scale.
2. Also the L-carnitine produced would require thorough purification to separate it from bacterial metabolites and contaminants which could be toxic and entail health hazards.

Moreover, NADH (an expensive reactant) would not stimulate the reaction when intact bacteria were used, because it would not penetrate the bacterial cell wall.

The present invention provides a process for enzymatically producing L-carnitine exclusively, which is not based on the use of bacteria as the source for the enzyme system to be used in the process.

The present invention is based on the discovery that the spores of the *Neurospora crassa* possess an hydroxylase enzyme which, when contacted with γ-butyrobetaine in a hydroxyl group donor solvent in the presence of sodium-2-oxoglutarate, ferrous ions and a reducing agent, selectively converts γ-butyrobetaine into substantially pure L-carnitine exclusively.

γ-butyrobetaine, $(CH_3)N—CH_2—CH_2—CH_2—COOH$, is a known compound and can be easily prepared by chemical synthesis. A method for producing γ-butyrobetaine is for instance disclosed in Can. J.

Chem 54 (1976) 3310–3311. The disclosures of this article are incorporated herein by reference.

Hydroxylation of γ-butyrobetaine into L-carnitine is known to occur in living organisms. In fact, research over the past few years has definitely ascertained that the biosynthetic pathway of carnitine is as follows:

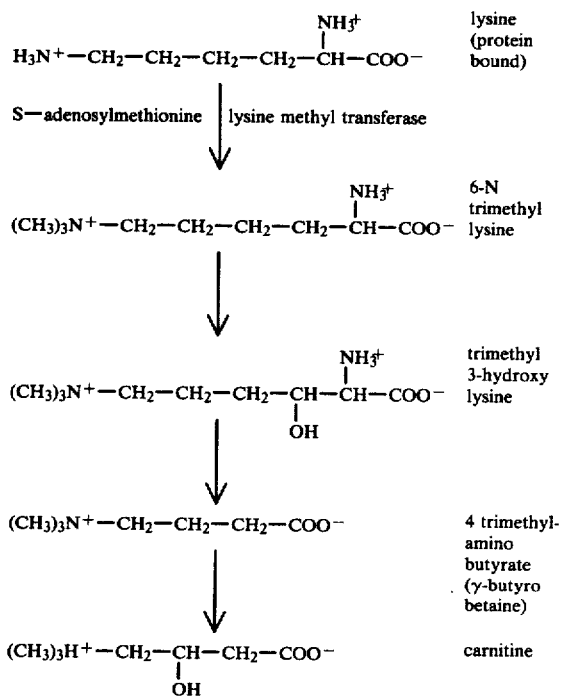

Hydroxylation of γ-butyrobetaine into L-carnitine by a partially purified soluble protein fraction isolated from rat liver, has been also disclosed. See Biochemistry, vol. 6, No. 5 May, 1967, 1271—1282.

It has been never previously disclosed, however, that a γ-butyrobetaine hydroxylase enzyme is present in the spores of Neurospora crassa and that this hydroxylase enzyme can be released (so as to be available for the γ-butyrobetaine conversion) by a treatment of the spores which induces a modification of the structure thereof.

According to the invention, the process for producing L-carnitine is based on the reaction of γ-butyrobetaine with a hydroxylase enzyme, and is characterized in that it comprises the step of contacting with a phase comprising the release products of the spores of the mold Neurospora crassa a solution in a hydroxyl group donor solvent of (a) γ-butyrobetaine;
(b) sodium-2-oxoglutarate;
(c) a reducing agent; and
(d) a ferrous ion source as hydroxylation catalyst.

The spore release products-containing phase is obtained either by chemico-phisically treating the spores with a detergent or by subjecting the spores to a mechanical treatment, e.g. with ultrasonic disintegrator.

Preferably, with a view to optimizing the L-carnitine yield, the solution also comprises (e) catalase.

Solvent

The solvent wherein γ-butyrobetaine, sodium-2-oxoglutarate, the reducing agent and the hydroxylation catalyst are dissolved is selected from the group comprising water, buffer solutions, lower alkanols having from 1 to 4 carbon atoms and mixture thereof.

A potassium phosphate buffer solution at pH 7 is the preferred solvent.

Reducing Agent

The reducing agent for use in the process of the present invention is any reductant suitable for reducing ferric ions ($Fe^{+3}$) into ferrous ions ($Fe^{+2}$). These latter act as the catalyst of the hydroxylation reaction of γ-butyrobetaine by the hydroxylase enzyme contained in the spores of Neurospora crassa. Consequently, any ferric ion which might be formed, should be promptly converted again into the oxydation state +2.

Non limiting examples of suitable reducing agents are the alkali metal dithionites, ascorbic acid and the alkali metal salts thereof.

Ferrous ion source

As a source of ferrous ions, any water soluble ferrous salt the anion moiety whereof does not inactivate the hydroxylase enzyme activity, might be used.

Suitable ferrous salts are $FeSO_4$, $(NH_4)_2Fe(SO_4)_2$ and $Fe(SCN)_2$, the former compound being particularly preferred.

Spores.

Although the spores of any strain of Neurospora crassa might be advantageously used in the process of this invention, it has been found that the strains ATCC 9279, ATCC 13837, ATCC 15514 and ATCC 24924 are particularly preferred.

The procedures for growing, isolating and purifying the spores of Neurospora crassa fall within the normal skill of any average expert in the mycological techniques.

However, a preferred one is the procedure disclosed by M. Cortat et al. in "Conidiation of Neurospora Crassa in Submerged Culture without Mycelial Phase", Arch. Microbiol. 95, 305–309 (1974).

The thus grown and isolated spores can be stored indefinively without any loss or substantial decrease in their enzyme activity.

Spore treatment

The spores are treated either with a detergent, such as TRITON X-100, or with mechanical devices, particularly ultrasonic disintegrators. These treatments release the hydroxylation enzyme and provide a hydroxylation enzyme-containing phase which may or may not contain the remnants of the treated spores and is used in the process of this invention.

Measurement of γ-butyrobetaine hydroxylase activity.

γ-butyrobetaine hydroxylase activity is measured in a reaction vessel containing an amount of the phase comprising the spore modification products sufficient to give an enzyme concentration of about 5-30 p moles/ml, γ-butyrobetaine (2–14 mM), $(NH_4)_2Fe(SO_4)_2$ (0.6–2 mM), sodium ascorbate (10–14 mM), sodium 2-oxoglutarate (1.4–3 mM), catalase (1–1.4 g/l) in potassium phosphate buffer (14 mM) at pH 7.

After 30–60 min. incubation at 37° C. the reaction mixture is filtered through 0.7μ MILLIPORE filters in order to remove the spores and the filtrate analyzed for L-carnitine by the method of David J. Pearson et al., "Methods of Enzymatic Analysis", Vol. 4 (2nd edition), 1974, pag. 1758, Academic Press, Inc.

The sample under examination is tested against a control containing the same components except that no γ-butyrobetaine is added.

In order to separate any unreacted γ-butyrobetaine from L-carnitine, a preferred one is the procedure disclosed by Göran Lindstedt in Biochemistry, vol. 6, no. 5, May 1967, pag. 1271–1282.

From the foregoing it is apparent that the enzymatic process of the present invention allows several advantages over the prior art processes to be achieved.

Some of these advantages are listed hereinbelow:

(1) Over the chemical processes of the prior art (which, as already indicated hereinabove, all produce racemic mixtures of both D and L carnitine) the process of this invention presents the advantage of producing exclusively substantially pure L-carnitine in high yield (about 80%). The resolution of the racemate into the laevorotatory and dextrorotatory form and the subsequent conversion of this latter into D,L-carnitine to be again submitted to resolution, is thus totally avoided.

(2) Over the prior art enzymatic process based on the use of bacteria as the source for the enzyme to be used in the process, the process of this invention presents the advantage that no cumbersome and expensive purification procedures have to be carried out on either the enzyme to be used or the L-carnitine produced. The hydroxylase enzyme does not even need to be isolated from the spore preparation which can be safely used as such and the L-carnitine produced is recovered in substantially pure, crystallized form. Conversely, with the enzymatic methods based on bacteria, both the enzyme and, above all, the L-carnitine would require extensive purification to avoid contamination by bacteria and bacterial metabolites.

(3) The *Neurospora crassa* spores can be prepared in large quantities and stored in dry form. They can be used whenever desired without significant loss of enzyme activity.

What is claimed is:

1. A process for the preparation of L-carnitine which comprises contacting γ-butyrobetaine in the presence of sodium 2-oxoglutarate, a reducing agent, a source of ferrous ions and a hydroxyl group donor solvent, with a source of the hydroxylase enzyme released from the spores of *Neurospora crassa*.

2. The process of claim 1 wherein catalase is also present in the reaction mixture.

3. The process of claim 1 wherein said hydroxyl group donor solvent is selected from the group comprising water, buffer solutions, a lower alkanol of from 1 to 4 carbon atoms and mixtures thereof.

4. The process of claim 1, wherein said reducing agent is selected from the group comprising an alkali metal dithionite, ascorbic acid and the alkali metal salts thereof.

5. The process of claim 1, wherein said ferrous ion source is selected from the group comprising $FeSO_4$, $(NH_4)_2Fe(SO_4)_2$ and $Fe(SCN)_2$.

6. The process of claim 1, wherein said *Neurospora crassa* is selected from the group comprising the strains ATCC 13837, ATCC 24914, ATCC 9279 and ATCC 15514.

7. The process of claim 1 wherein said hydroxylase enzyme is obtained by treating said spores with a detergent.

8. The process of claim 7 wherein said detergent is TRITON X-100.

9. The process of claim 1 wherein said hydroxylase enzyme is obtained by subjecting said spores to ultrasonic disruption.

* * * * *